United States Patent
Kobayashi

(10) Patent No.: US 7,122,499 B2
(45) Date of Patent: Oct. 17, 2006

(54) OSMIUM OXIDE CARRIED BY HYDROPHILIC POLYMER

(75) Inventor: Shu Kobayashi, 1-6-6-702, Sarugakucho, Chiyoda-ku, Tokyo 101-0064 (JP)

(73) Assignees: Shu Kobayashi, Tokyo (JP); Wako Pure Chemical Industries, Ltd., Osaka (JP)

( * ) Notice: Subject to any disclaimer, the term of this patent is extended or adjusted under 35 U.S.C. 154(b) by 164 days.

(21) Appl. No.: 10/469,238

(22) PCT Filed: Mar. 8, 2002

(86) PCT No.: PCT/JP02/02179

§ 371 (c)(1),
(2), (4) Date: Sep. 5, 2003

(87) PCT Pub. No.: WO02/072259

PCT Pub. Date: Sep. 19, 2002

(65) Prior Publication Data

US 2004/0092779 A1    May 13, 2004

(30) Foreign Application Priority Data

Mar. 9, 2001    (JP) ............... 2001-66241

(51) Int. Cl.
*B01J 31/00*    (2006.01)
*B01J 23/40*    (2006.01)
*B01J 23/42*    (2006.01)
*C07C 45/00*    (2006.01)
*C07C 29/04*    (2006.01)

(52) U.S. Cl. .............. 502/159; 502/172; 502/326; 568/426; 568/896; 568/900

(58) Field of Classification Search ........... 502/172, 502/159, 326; 568/426, 896, 900
See application file for complete search history.

(56) References Cited

U.S. PATENT DOCUMENTS 2,224,837 A * 12/1940 Rosenthal et al. ........... 528/205
2,534,304 A * 12/1950 Serniuk et al. ............. 560/247
4,478,983 A * 10/1984 Parker ...................... 525/332.2
6,297,186 B1 * 10/2001 Kobayashi ................. 502/159
6,800,583 B1 * 10/2004 Grosch et al. .............. 502/175
6,878,661 B1 *  4/2005 Ooms et al. ................ 502/152

FOREIGN PATENT DOCUMENTS

| EP | 0252254 | 1/1988 |
| EP | 0940170 | 9/1999 |
| JP | 11-314038 | 11/1999 |

OTHER PUBLICATIONS

W. Herrmann et al., J. Molec. Catalysis A: Chemical, vol. 120 (1997), pp. 197-205.*
Kobayashi et al, "Catalytic Asymmetric Dihydroxylation . . . Osmium Tetroxide", Org. Lett., Aug. 23, 2001, vol. 3, No. 17, pp. 2649-2652.
Tasku Ishida et al, "Shinki Micro Capsule-ka . . . Dihydroxyl-ka Hanno no Kaihatsu", CSJ: The Chem. Soc. of Japan 79th Shunki Nenkai Koen Yokoshu, (Mar. 15, 2001), vol. 79, No. 2, p. 1141.
Kobayashi et al, "Catalytic Asymmetric Dihydroxylation of Olefins . . . Osmium Catalyst", J. Am. Chem. Soc. 1999, vol. 121, No. 48, pp. 11229-11230.
Cainelli et al, "Cleavage of Olefins . . . Sodium Periodate", Synthesis 1989, No. 1 pp. 47-48.
International Search Report dated May 21, 2002.
Kobayashi et al; "New Methods for high-throughput synthesis"; XP-002315143; Pure and Applied Chemistry 73 (2001); pp. 1103-1111.
European Search Report dated Feb. 14, 2005.

* cited by examiner

*Primary Examiner*—Karl Group
*Assistant Examiner*—J. Pasterczyk
(74) *Attorney, Agent, or Firm*—Armstrong, Kratz, Quintos, Hanson & Brooks, LLP

(57) ABSTRACT

A carrier for carrying an osmium oxide comprising an aromatic polyolefin polymer having a group shown by the general formula [1] as a substituent on the aromatic ring of said polyolefin polymer:

—A'—O(—A—O)$_n$—R[1]

(wherein A is an alkylene group; A' is a direct link or an alkylene group; R is an aryl group; and n is an integer of 1 to 10), an osmium oxide carried by the carrier for carrying an osmium oxide and a method for producing the osmium oxide carried by said carrier are disclosed. Since the osmium oxide carried by the carrier of the present invention has a hydrophilic group, in an oxidation reaction and an asymmetric oxidation reaction, particularly in a heterogeneous solvent system, the osmium oxide carried by the carrier of the present invention enables to produce a diol compound easily and in a high optical yield.

14 Claims, No Drawings

OSMIUM OXIDE CARRIED BY HYDROPHILIC POLYMER

FIELD OF THE INVENTION

The present invention relates to an osmium oxide composition carried by an aromatic polyolefin having a specific substituent, which enables to perform an oxidation of an organic compound by an osmium oxide on an industrial production scale.

BACKGROUND OF THE INVENTION

Although it is said that osmium oxides existing solely and firmly are oxides of osmium of 4 and 8 valences, but osmium oxides of 2, 3 and 6 valences can also exist.

An osmium oxide of 8 valences is usually called "osmium tetroxide", or "osmic acid" in the case of an aqueous solution, and known as a superior oxidizing agent or catalyst in an organic synthetic reaction due to a great oxidizing ability thereof. On the other hand, however, it is also well known that osmium tetroxide is of high toxicity and sublimation character, having an offensive odor perceptible even at an extremely low concentration such as $2 \times 10^{-5}$ mg/ml, and offending a mucous membrane of eyes or affecting adversely upon general respiratory organs with vapor thereof. Therefore, so far osmium tetroxide has been only used as an oxidizing agent for oxidizing a small amount of precious substance due to many problems in an industrial use thereof. In this connection, several attempts have been made to use osmium tetroxide safely for an industrial use.

For instance, a process for manufacturing catalysts based on nitrogen-containing polymers on which osmium oxide is precipitated from a solvent has been described in JP-A-4-505884, and actually a commercial product of about 1% by weight of osmium tetroxide carried on poly(4-vinylpyridine) (for instance, the one listed up in a catalogue of Sigma-Aldrich Corp.) is on the market.

However, it was not necessarily easy to produce an osmium tetroxide compound by said method, because said method always utilized a chemical bonding of an osmium oxide to a quaternary nitrogen atom, using a basic polymer having a nitrogen atom, in particular, a cross-linked polymer thereof. In addition, there was another problem that a polymer itself carrying said osmium oxide gradually decomposed when an osmium oxide compound obtained by said method was used as an oxidizing agent under an oxidative condition (Journal of Molecular Catalysis A: Chemical Vol. 120(1997), page 203 right column).

Furthermore, the osmium oxide in the osmium oxide compound disclosed in the above JP-A-4-505884 is not necessarily stably carried as osmium tetroxide, and is evidently inferior in a function as an oxidizing agent to that of osmium tetroxide itself, because it does not exist as osmium tetroxide, but as osmium trioxide or sometimes in a reduced state such as an oxide of a polymer or an oxo anion.

On the other hand, it has been lately reported that an optically active compound can be obtained by using an optically active ligand together with osmium tetroxide in a dihydroxylation reaction using osmium tetroxide in "Catalytic Asymmetric Snthesis" ed. by I. Ojima, VHC Publisher, New York, 1993, page 227–272; Chem. Rev., 94, 2483–2547(1994) and the like. However, it is difficult to recover and reuse osmium tetroxide from the viewpoint of safety in handling and the like because osmium tetroxide used in these asymmetric oxidation reactions is employed as it is, without being carried on a polymer or the like.

Furthermore, a polymer complex in which osmium tetroxide is coordinated with optically active ligands introduced into the polymer, and an asymmetric reaction using the above complex have been reported in Eur. J. Org. Chem., 1981, 21–27 and the like, but many problems are remaining unsolved in the production of such an osmium tetroxide compound, because it is not easy to produce a polymer itself in which an optically active ligand is introduced, and the polymer is necessary to be further reacted with osmium tetroxide. In addition, there is another problem that osmium tetroxide coordinated to the ligands gradually drops off during a reaction and cannot be reused.

Moreover, it has been attempted to make handling of an osmium oxide easy and improve solvent resistance thereof by microcapsulating said osmium oxide such as osmium tetroxide which is not easy to handle due to strong toxicity, using an olefin-based polymer such as polystyrene (JP-A-11-314038). Although this microcapsulated osmium tetroxide enabled use for an asymmetric dihydroxylation reaction due to an improved solvent resistance, it was used only for a reaction in a homogeneous solvent system, and in addition it was necessary to react a substrate gradually so as to strictly control the asymmetric reaction.

It is known that a heterogeneous asymmetric dihydroxylation reaction using potassium ferricyanide or the like as a co-oxidizing agent does not require a gradual addition of substrate to the reaction system, and therefore gives a high optical yield in a short reaction time, while an asymmetric dihydroxylation reaction in a homogeneous solvent system generally requires a gradual addition of substrate to the reaction system so as to obtain a high optical yield.

Thus, it has been desired to create a new compound to carry osmium oxide as an oxidizing agent that enables an asymmetric dihydroxylation reaction in a heterogeneous solvent system where a conventional operation or the like to control an asymmetric reaction is not required.

DISCLOSURES OF THE INVENTION

The present invention has been made considering the above-described situations. An object of the present invention is to provide a compound to carry an osmium oxide with a superior solvent and heat resistances that act effectively as a catalyst for a reaction in a heterogeneous solvent system and prevents the osmium oxide from eluting therefrom even in repeated uses.

The present inventors, after an extensive study to fulfill the above purpose, have found out that an osmium oxide carried by an aromatic polyolefin with a specific substituent in a side chain thereof has an improved hydrophilic property and acts effectively as an oxidizing agent even in a heterogeneous solvent system (mixed solvent system), and accomplished the present invention.

The present invention provides a carrier for carrying an osmium oxide comprising an aromatic polyolefin having a group shown by the general formula [1]:

—A'—O(—A—O)$_n$—R  [1]

(wherein, A is an alkylene group; A' is a bond or an alkylene group; R is an aryl group; and n is an integer of 1 to 10), an osmium oxide carried by said carrier for carrying an osmium oxide and a method for producing said osmium oxide carried by the carrier.

Further, the present invention provides an oxidizing agent comprising the osmium oxide carried by the carrier and a method for producing a corresponding diol compound which comprises reacting a compound having a reactive double bond with the oxidizing agent.

Still further, the present invention provides a method for producing a corresponding carbonyl compound which comprises reacting a compound having a reactive double bond with the oxidizing agent and a strong oxidizing agent.

BEST MODE FOR CARRYING OUT THE INVENTION

The osmium oxide according to the present invention includes, for instance, osmium dioxide and osmium tetroxide, preferably osmium tetroxide.

A part of the osmium oxide carried on an aromatic polyolefin by a production method of the present invention is reduced by a small amount of unreacted unsaturated bonds usually remaining in the aromatic polyolefin and such osmium oxide which is partially reduced is also included in the osmium oxide of the present invention.

The alkylene group shown by A or A' in the general formula [1] may be straight chained, branched or cyclic, and includes usually those having 1 to 6 carbon atoms, preferably those having 1 to 3 carbon atoms, and specifically a group such as methylene, ethylene, propylene, trimethylene, tetramethylene, pentamethylene, hexamethylene, ethylethylene, 1-methyltrimethylene, 2-methyltrimethylene, 2-ethyltrimethylene, 1-methyltetramethylene, 2-methyltetramethylene, 1-ethyltetramethylene, 2-methyltetramethylene, 1-methylpentamethylene, 2-methylpentamethylene, 3-methylpentamethylene, cyclopropylene, cyclopentylene and cyclohexylene, and preferably a linear group among them.

The aryl group shown by R includes, for instance, a group such as phenyl and naphthyl.

n is an integer of usually 1 to 10, preferably 1 to 5, more preferably 1 to 3 and most preferably 1.

The aromatic polyolefin having a group shown by the general formula [1] that constitutes a carrier for carrying an osmium oxide according to the present invention (hereinafter abbreviated to a carrier of the present invention) may be those having one or more aromatic rings which have a group shown by the general formula [1] at an arbitrary position in the polymer molecule, and specifically includes, for instance, a homopolymer of an aromatic olefin compound having group(s) shown by the general formula [1] of usually 1 to 5, preferably 1 to 2 and more preferably 1 at an arbitrary position of the aromatic ring thereof, a copolymer of said aromatic olefin compound and an aromatic olefin compound not having any group shown by the general formula [1] and/or other polymerizable monomer.

The aromatic olefin compound having a group shown by the general formula [1] at an arbitrary position in the aromatic ring as a substituent and an aromatic olefin compound not having any group shown by the general formula [1] include, for instance, a styrene-type compound that may have an alkyl group of usually 1 to 4 carbon atoms as a substituent at the α-position thereof, and specifically, for instance, styrene, α-methylstyrene, α-ethylstyrene, α-propylstyrene, α-isopropylstyrene, α-butylstyrene, α-isobutylstyrene and α-tert-butylstyrene.

The aromatic ring of the carrier of the present invention may have further one or more groups as a substituent other than a group shown by the general formula [1], for instance, a halogen atom such as a chlorine atom, a bromine atom and a fluorine atom, an alkyl group of usually 1 to 6 carbon atoms and preferably 1 to 3 carbon atoms such as methyl, ethyl and propyl, an alkoxy group of usually 1 to 6 carbon atoms and preferably 1 to 3 carbon atoms such as methoxy, ethoxy and propoxy.

Specific examples of other polymerizable monomers include, for instance, ethylenically unsaturated aliphatic hydrocarbons of 2 to 20 carbon atoms such as ethylene, propylene, butylene and isobutylene; alkenyl esters of 3 to 20 carbon atoms such as vinyl formate, vinyl acetate, vinyl propionate and isopropenyl acetate; halogen-containing ethylenically unsaturated compounds of 2 to 20 carbon atoms such as vinyl chloride, vinylidene chloride, vinylidene fluoride and tetrafluoroethylene; ethylenically unsaturated carboxylic acids of 3 to 20 carbon atoms such as acrylic acid, methacrylic acid, itaconic acid, maleic acid, fumaric acid, crotonic acid, 3-butenoic acid, 4-pentenoic acid and vinyl benzoic acid (these acids may form a salt of an alkali metal such as sodium and potassium, or an ammonium ion); ethylenically unsaturated carboxylic esters such as methyl methacrylate, ethyl methacrylate, propyl methacrylate, butyl methacrylate, 2-ethylhexyl methacrylate, methyl acrylate, ethyl acrylate, butyl acrylate, 2-ethylhexyl acrylate, lauryl methacrylate, stearyl acrylate, methyl itaconate, ethyl itaconate, methyl maleate, ethyl maleate, methyl fumalate, ethyl fumalate, methyl crotonate, ethyl crotonate and methyl 3-butenoate; cyano-containing ethylenically unsaturated compounds of 3 to 20 carbon atoms such as acrylonitrile, methacrylonitrile and allyl cyanide; ethylenically unsaturated amide compounds of 3 to 20 carbon atoms such as acrylamide and methacrylamide; ethylenically unsaturated aldehydes of 3 to 20 carbon atoms such as acrolein and crotonic aldehyde; ethylenically unsaturated aliphatic heterocyclic amines of 5 to 20 carbon atoms such as N-vinylpyrrolidone and vinylpiperidine; and ethylenically unsaturated aromatic heterocyclic amines of 5 to 20 carbon atoms such as vinylpyridine and 1-vinylimidazole.

A weight average molecular weight of the carrier of the present invention ranges usually from 10,000 to 500,000, preferably from 20,000 to 100,000, and a degree of polymerization thereof ranges from 100 to 5,000, preferably from 200 to 1,000.

When the carrier of the present invention is composed of a copolymer of an aromatic olefin compound having a group shown by the general formula [1] and an aromatic olefin compound not having a group shown by the general formula [1], a number of aromatic ring having a group shown by the general formula [1] ranges from 1 to 30%, preferably from 1 to 10% of a number of total aromatic rings in the polymer.

When the carrier of the present invention is composed of a copolymer of an aromatic olefin compound having a group shown by the general formula [1] and other polymerizable monomer, an unit having an aromatic ring accounts for usually 30% or more, preferably 50 to 90% of a total units in the polymer, and a number of aromatic rings having a group shown by the general formula [1] ranges from 1 to 30%, preferably from 1 to 10% of the number of total aromatic rings in the polymer.

Further, when the carrier of the present invention is composed of a copolymer of an aromatic olefin compound having a group shown by the general formula [1], an aromatic olefin compound not having a group shown by the general formula [1] and other polymerizable monomer, an unit having an aromatic ring accounts for usually 30% or more, preferably 50 to 90% of a total units of the polymer, and a number of aromatic rings having a group shown by the general formula [1] ranges from 1 to 30%, preferably from 1 to 10% of the number of total aromatic rings in the polymer.

In order to produce the carrier of the present invention, for instance, the aromatic olefin compound having a group shown by the general formula [1] as a substituent in the aromatic ring thereof may be polymerized in accordance with an ordinary method, or, for instance, a aromatic olefin compound having a group shown by the general formula [1] as a substituent in the aromatic ring thereof, and an aromatic olefin compound not having a group shown by the general formula [1] and/or other polymerizable monomer may be copolymerized in accordance with an ordinary method.

Further, a polymer obtained by polymerizing or copolymerizing as described above an aromatic olefin compound having a halogen atom such as a chlorine atom as a substituent in the aromatic ring thereof, instead of an aromatic olefin compound having a group shown by the general formula [1] as a substituent in the aromatic ring thereof can also be reacted with an alcohol compound corresponding to a group shown by the general formula [1] to obtain a carrier of the present invention.

The alcohol compound corresponding to a group shown by the general formula [1] includes: for instance, when A' of the general formula [1] is a bond, a compound shown by the general formula [4]:

HO—(A—O—)$_n$—R    [4]

(wherein, A, R and n are the same as defined above); and when A' of the general formula [1] is an alkylene group, and a compound shown by the general formula [5]:

HO—X—O—(A—O—)$_n$—R    [5]

(wherein, X is an alkylene group; and A, R and n are the same as defined above).

The alkylene group shown by X in the above general formula [5] includes the same group as shown by above A or A'.

In order to make a carrier of the present invention to carry an osmium oxide, a so-called microcapsulating technology for a substance of relatively large molecular weight that is prevalent, for instance, in the field of medicine or food, may be applied, and a carrier of the present invention and an osmium oxide may be reacted by contacting each other according to, for instance, a method described as a summary in Pharmaceutica Acta Helvetiae vol. 53 (1978) page 17–23 and page 33–39.

Namely, an osmium oxide carried by a carrier of the present invention can be obtained by, for instance, dissolving a carrier of the present invention in a proper organic solvent, then adding an osmium oxide while heating if necessary followed by stirring and reacting the solution to obtain a homogeneous solution, cooling the reaction mixture after completion of the reaction, and on appearance of deposits, solidifying the deposits by adding a suitable poor solvent to the reaction mixture, then filtrating and drying.

The organic solvent to dissolve a carrier of the present invention includes aromatic hydrocarbons such as benzene, toluene and xylene; ketones such as methyl ethyl ketone; esters such as ethyl acetate; halogenated hydrocarbons such as chloroform, dichloroethane and carbon tetrachloride; saturated cyclic hydrocarbons such as cyclohexane; and ethers such as diethyl ether and tetrahydrofuran. These organic solvents may be used alone or in a proper combination of two or more kinds thereof, and selected properly depending on a kind of a carrier of the present invention to be dissolved.

The poor solvent to be added after reaction includes lower alcohols such as methanol and ethanol, and aliphatic hydrocarbons such as n-hexane. These poor solvents are properly selected depending on a kind of a carrier of the present invention used for reaction.

An amount of the carrier of the present invention to be used is determined so that an amount of aromatic ring in the carrier is usually 1 to 10,000 times by mole, preferably 5 to 100 times by mole of the osmium oxide to be used.

An amount of the organic solvent to dissolve a carrier of the present invention is usually 1 to 100 times by weight, preferably 2 to 20 times by weight of the carrier of the present invention.

A reaction temperature is usually 0 to 150° C., preferably 10 to 100° C. and more preferably 25 to 80° C.

A reaction time is usually 10 minutes to 5 hours, preferably 30 minutes to 2 hours.

The thus obtained osmium oxide carried by the carrier of the present invention is considered to be present in a state being microcapsulated by the carrier of the present invention. In other words, it is estimated that the osmium oxide is carried in the carrier of the present invention or on its surface by an electronic interaction between a vacant orbit of an osmium atom of the osmium oxide and a π-bond in an aromatic ring of the carrier of the present invention.

An amount of the osmium oxide which can be carried by the carrier of the present invention is usually 10% (w/w) to 20% (w/w) based on the carrier.

The osmium oxide carried by the carrier of the present invention may take any shape such as a lump(block) and fine particles. Fine particles are preferable from the viewpoints of easy handling and a performance as an oxidizing agent, but even a lump can be practically used by crushing properly.

When the osmium oxide carried by the carrier of the present invention is the fine particle, the average particle size of the fine particles is usually 0.1 to 1,000 μm, preferably 100 to 200 μm.

The osmium oxide carried by the carrier of the present invention is not only useful as a catalyst for various reactions, but also stable for a long period of 12 or more months in exhibiting the performance of osmium oxide itself, and further can maintain an activity thereof even in repeated use due to superior durability and solvent resistance thereof. Moreover, an activity of the osmium oxide is not lowered even by using many times repeatedly if it is used in combination with a suitable co-oxidizing agent.

The osmium oxide carried by the carrier of the present invention can be efficiently handled without paying special attention to toxicity and odor possessed by the osmium oxide and quantitatively recovered as a catalyst after used, because the osmium oxide is carried by the carrier of the present invention.

These characteristics suggest that the osmium oxide is probably enshrouded(microcapsulated) or covered by a substrate polymer, and therefore an effect thereof such as an effect as an oxidizing agent is maintained without collapsing its structure, during storage or even after used as an oxidizing agent. Further, although fine particles of the osmium oxide carried by the carrier of the present invention are microcapsulated or enshrouded by a substrate polymer, the microcapsule or the state of enshrouding is not perfect, but it has pores and interstices which make the osmium oxide contact to the air (Pharmaceutica Acta Helvetiae, vol. 53 (1978), page 17–23 and page 33–39). Therefore, it is supposed from the above situation that the osmium oxide carried by a substrate polymer is not entirely blocked from the atmosphere.

With these superior characteristics, the osmium oxide carried by the carrier of the present invention can be used advantageously as a catalyst of various chemical reactions on an industrial scale. Above all, it can be effectively used as an oxidizing catalyst or an oxidizing agent to oxidize a compound having a reactive double bond(s) to form a diol compound or a carbonyl compound.

When the oxidizing agent of the present invention is reacted with a reactive double bond, a double bond site having a reactive activity is cleaved, two hydroxyl groups are introduced to form a corresponding diol compound.

The compound having a reactive double bond may be any compound as long as it has a reactive double bond(s) in a molecule, and includes, for instance, not only an olefin, a diene compound and an unsaturated cyclic hydrocarbon compound, but also a polymer and a compound having any functional group and/or aromatic ring as a substituent as long as it has one or more reactive double bonds in a molecule.

Using an olefin as an example of a compound having a reactive double bond, a method for forming a diol compound from said olefin using the oxidizing agent of the present invention will be described hereinbelow.

An olefin compound, for instance, a compound shown by the general formula [6]:

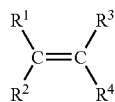

[6]

(wherein, $R^1$, $R^2$, $R^3$ and $R^4$ are each independently a hydrogen atom, an alkyl group, an aryl group and an aralkyl group.) is mixed with a proper solvent, and then the osmium oxide carried by the carrier of the present invention are added thereto, if necessary with a co-oxidizing agent, and followed by reacting them to obtain a diol compound shown by the general formula [7] below:

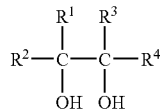

[7]

(wherein, $R^1$ to $R^4$ are the same as above).

The alkyl group shown by $R^1$ to $R^4$ in the general formulas [6] and [7] may be straight chained, branched or cyclic, and includes usually a group having one or more carbon atoms, preferably a group of 1 to 20 carbon atoms, more preferably a group of 1 to 10 carbon atoms, still more preferably a group of 1 to 6 carbon atoms, which is specifically exemplified by a group such as methyl, ethyl, n-propyl, isopropyl, n-butyl, isobutyl, sec-butyl, tert-butyl, n-pentyl, isopentyl, sec-pentyl, tert-pentyl, neopentyl, n-hexyl, isohexyl, sec-hexyl, tert-hexyl, n-heptyl, isoheptyl, sec-heptyl, tert-heptyl, n-octyl, sec-octyl, tert-octyl, nonyl, decyl, undecyl, dodecyl, tridecyl, tetradecyl, pentadecyl, hexadecyl, heptadecyl, octa-decyl, nonadecyl, icosyl, docosyl, tetracosyl, pentacosyl, heptacosyl, triacontyl, dotriacontyl, hexacontyl, octacontyl, cyclopropyl, cyclopentyl, cyclohexyl, cycloheptyl, cyclooc-tyl, cyclononyl, cyclodecyl, cycloundecyl, cyclododecyl, cyclotridecyl, cyclotetradecyl, cyclopentadecyl, cyclohexa-decyl, cycloheptadecyl, cyclooctadecyl, cyclononyl and cycloicosyl.

The aryl group includes usually a group having 6 to 14 carbon atoms, which is specifically exemplified by a group such as phenylene, naphthylene, anthracenediyl and phenan-thracenediyl.

The aralkyl group includes usually a group having 7 to 10 carbon atoms, which is specifically exemplified by a group such as benzyl, phenylethyl, phenylpropyl and phenylbutyl.

An amount of the osmium oxide carried by the carrier of the present invention to be used is determined so that an amount of the osmium oxide carried becomes usually 0.001 to 0.3 times by mole, preferably 0.01 to 0.05 times by mole of an amount of olefin to be used.

The solvent for reaction includes alcohols such as metha-nol, ethanol, n-propanol, isopropanol, n-butanol, isobutanol, sec-butanol and tert-butanol; ketones such as acetone and methyl ethyl ketone; ethers such as diethyl ether, 1,4-dioxane and tetrahydrofuran; esters such as ethyl acetate; hydrocarbons such as benzene, toluene, xylene and cyclo-hexane; halogenated hydrocarbons such as chloroform, dichloroethane and carbon tetrachloride; nitriles such as acetonitrile and butylonitrile; water-soluble organic solvents such as tetrahydrofuran; N,N-dimethylformamide; dimeth-ylsulfoxide; water, etc. These solvents may be used alone or in a proper combination of two or more kinds thereof, and a combination of water and one or more kinds of water-soluble organic solvents is preferable above all. A specific example of a preferable combination includes, for instance, water-acetone, water-acetonitrile, water-acetonitrile-ac-etone, water-tert-butanol and the like. A ratio of water to water-soluble organic solvent(s) in a combination of water and water-soluble organic solvent(s) is usually 1 to 50%, preferably 10 to 30%.

An amount of the solvent for reaction to be used is usually 1 to 50 times by weight, preferably 1 to 20 times by weight and more preferably 3 to 15 times by weight of an amount of an olefin substrate.

The co-oxidizing agent includes, for instantce, N-oxides such as 4-methylmorpholine-N-oxide, trimethylamine-N-oxide, triethylamine-N-oxide, pyridine-N-oxide, α-picoline-N-oxide, β-picoline-N-oxide and γ-picoline-N-oxide; perox-ides such as hydrogen peroxide, tert-butyl hydroperoxide, acetyl hydroperoxide, tert-butyl peroxide, benzoyl peroxide, tert-butyl peracetate, tert-butyl perbenzoate, tert-butylper-oxyisopropyl carbonate; periodates such as potassium perio-date and sodium periodate; persulfates such as potassium persulfate, sodium persulfate and ammonium persulfate; peroxides such as methachloroperbenzoate; hypochlorites such as sodium hypochlorite, potassium hypochlorite and ammonium hypochlorite; potassium ferricyanide; and oxy-gen.

An amount of the co-oxidizing agent to be used is usually 1 to 5 times by mole, preferably 1 to 3 times by mole of amount of an olefin substrate.

A reaction time is usually 5 minutes to 36 hours, prefer-ably 10 minutes to 16 hours and more preferably 1 to 6 hours.

A reaction temperature is usually −10 to 100° C., prefer-ably 10 to 80° C. and more preferably 15 to 40° C.

In particular, when the olefin shown by the general formula [6] is an asymmetric olefin with respect to the reactive double bond where $R^1$ and $R^2$ as well as $R^3$ and $R^4$ are each different group from each other, or a trans-form of symmetric olefin, the above reaction in the coexistence of an asymmetric ligand provides an asymmetric oxidation reac-tion, to produce a corresponding diol compound with a high stereoselectivity.

The asymmetric ligand includes, for instance, 1,4-bis (9-o-dihydroquinidil) phthalazine, dihydroquinidine, dihyd-roquinine, dihydrocinchonine and dihydrocinchonidine.

An amount of the asymmetric ligand to be used is usually 0.001 to 0.3 times by mole, preferably 0.01 to 0.05 times by mole of the amount of olefin.

The osmium oxide carried by the carrier of the present invention has a hydrophilic group shown by the general formula [1] in a molecular structure of the carrier. Therefore, by using this, an objective optically active diol compound can be obtained in a high yield and a high optical yield even by adding a substrate at a time, in an asymmetric dihydroxylation reaction using a microcapsulated osmium oxide in a heterogeneous solvent system of a mixed solvent such as water-acetone, water-acetonitrile and water-tert-butanol that could be conventionally performed only by a gradual addition of the substrate.

Namely, the objective asymmetric diol compound can be obtained by adding, to a heterogeneous mixed solvent as described above, the oxidizing agent of the present invention, a proper asymmetric olefin or a trans-form of symmetric olefin, an asymmetric ligand suitable for the asymmetric dihydroxylation reaction, and a proper co-oxidizing agent, and if necessary further a proper base, and then reacting followed by an ordinary after-treatment.

The asymmetric ligand, The co-oxidizing agent and the like which are used for the above reaction may be suitably selected from above examples, and potassium ferricyanide is particularly preferable as a co-oxidizing agent.

The base to be added if necessary includes carbonates such as potassium carbonate, sodium carbonate, sodium hydrogencarbonate and potassium hydrogencarbonate; alkali metal hydroxides such as sodium hydroxide and potassium hydroxide; and organic bases such as pyridine. An amount thereof to be used is usually 1 to 5 times by mole, preferably 1 to 3 times by mole of the amount of olefin.

An each amount of the reagents to be used, a reaction time, a reaction temperature and the like may be suitably determined correspondingly to the dihydroxylation reaction of the olefin described above.

In addition, by reacting the osmium oxide carried by the carrier of the present invention with a compound having a reactive double bond together with a strong oxidizing agent such as a periodate, in a proper solvent, a corresponding carbonyl compound can be obtained easily in a high yield.

Using an olefin as an example of the compound having a reactive double bond, a method for forming the carbonyl compound from said olefin using an oxidizing agent of the present invention will be described hereinbelow.

For instance, the osmium oxide carried by the carrier of the present invention, the strong oxidizing agent and the olefin compound shown by the general formula [6]:

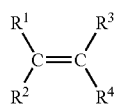

[6]

(wherein, $R^1$, $R^2$, $R^3$ and $R^4$ are the same as defined above) are mixed with a proper solvent, and then reacted to obtain the carbonyl compound shown by the general formula [8] below:

[8]

(wherein, $R^1$, $R^2$, $R^3$ and $R^4$ are the same as defined above) by cleavage of the double bond of the olefin.

The compound having a reactive double bond which is a substrate of the above carbonyl reaction includes the same as the compound having a reactive double bond which is a substrate of a dihydroxylation reaction of an olefin as described above.

The strong oxidizing agent includes periodates such as sodium periodate and potassium periodate.

An amount of the strong oxidizing agent to be used is 2 ore more times by mole, preferably 2 to 4 times by mole, more preferably 2.1 to 4 times by mole of the amount of the compound having a reactive double bond. That is, when an amount of the strong oxidizing agent to be used is not sufficient, there is little possibility for such a carbonyl-forming reaction by cleavage of an olefin to occur, and only a dihydroxylation reaction as described above occurs.

An amount of the osmium oxide carried by the carrier of the present invention to be used is determined so that an amount of the osmium oxide carried becomes usually 0.001 to 0.3 times by mole, preferably 0.01 to 0.05 times by mole of the amount of the compound having a reactive double bond used.

The solvent for the reaction may use any solvent that can be used for the dihydroxylation reaction of an olefin as described above can be used.

Other reaction conditions are the same as those for the dihydroxylation reaction of an olefin as described above.

The osmium oxide of the carrier of the present invention having a hydrophilic group in a molecular structure of the carrier as described above can fully exhibit a function as an oxidizing agent even in a water-soluble organic solvent or a mixed solvent such as water-acetone, water-acetonitrile and water-tert-butanol. Therefore, a carbonyl-forming reaction of an olefin using periodate or the like hardly soluble in a nonaqueous solvent, which was difficult with an osmium oxide microcapsulated with an olefin-based polymer as conventionally used, can be easily and safely performed by using the oxidizing agent of the present invention comprising the osmium oxide carried by the carrier of the present invention.

In addition, after completing a reaction using the osmium oxide carried by the carrier of the present invention as a catalyst, the osmium oxide carried by the carrier of the present invention can be reused as reaction catalyst without losing its activity, by separating from a reaction residue by filtration followed by drying.

The present invention will be further described by examples hereinbelow, but the present invention is not limited at all by these examples.

EXAMPLES

Example 1

Synthesis of the Carrier of the Present Invention (1) Synthesis of poly(styrene-co-p-chloromethylstyrene)

To 100 ml of chloroform were added 27.9 g (267.42 mmol) of styrene, 2.1 g (14.07 mmol) of p-chloromethylstyrene and 328.0 mg (2.0 mmol) of azobisbutylonitrile followed by allowing a polymerization for 48 hours while heating and refluxing at 80° C. After completion of the reaction, the reaction mixture was cooled to room temperature, then dropped into 500 ml of methanol cooled with ice, to solidify a desired polymer. The solidified polymer was filtrated and washed with methanol, and then dried for 24 hours using a vacuum pump, to obtain 30 g of poly (styreneco-p-chloromethylstyrene) in which 5 mol % of a chloromethyl group relative to the amount of styrene was introduced (yield 100%).

(2) Synthesis of the Carrier of the Present Invention in Which a 2-phenoxyethoxymethyl Group is Introduced.

With petroleum ether was washed 375.2 mg of sodium hydride and then dried under a reduced pressure. After drying, 972.0 mg of 2-phenoxy ethanol and 20 ml of tetrahydrofuran were added thereto in an ice bath and followed by reacting while stirring. After generation of hydrogen stopped, 5.0 g of the poly (styrene-co-p-chloromethylstyrene) obtained in the above (1) and 20 ml of tetrahydrofuran were added thereto and followed by reacting them for 20 hours while heating and refluxing at 90° C. After completion of the reaction, the reaction mixture was cooled down to room temperature by stop heating, then dropped into 500 ml of methanol cooled with ice to solidify a desired polymer. The solidified polymer was filtrated and added to 50 ml of cyclohexane, and then dissolved while stirring at 60° C. After dissolution, heating was stopped, and said solution was cooled down to room temperature, and then dropped into 500 ml of methanol cooled with ice to solidify the polymer. The solidified polymer was filtrated and washed with methanol, then dried for 24 hours under a reduced pressure, to obtain 5.9 g of the carrier of the present invention in which 5 mol % of a 2-phenoxyethoxymethyl group (—$CH_2OCH_2CH_2OPh$) relative to the amount of styrene was introduced (yield 100%).

Example 2

Synthesis of the Carrier of the Present Invention (1) Synthesis of 2-bromoethylphenyl ether To 3.25 ml (0.04 mmol) of pyridine were added 13.82 g (0.1 mol) of 2-phenoxy ethanol and 10.83 g (0.04 mol) of phosphorus tribromide, followed by reacting at 0° C. for 1 hour while stirring. The reaction solution was warmed up to 50° C. and then reacted for 1 hour while stirring. After completion of the reaction, excess 1N hydrochloric acid (0° C.) were added to the reaction solution and then subjected to an extraction procedure using chloroform. The resulting organic layer was washed with 1N hydrochloric acid, water and an aqueous solution of sodium hydrogen carbonate, then dried on magnesium sulfate and concentrated under a reduced pressure. An obtained crude product was purified by distillation to obtain 9.5 g of a desired 2-bromoethylphenyl ether (yield 47%).

(2) Synthesis of triethylene glycol monophenyl ether

To 8.5 ml (90 mmol) of diethylene glycol were added 840 mg (15 mmol) of potassium hydroxide and dissolved while stirring and heating at 120° C. in an oil bath. Heating was stopped after potassium hydroxide was completely dissolved, diethylene glycol was distilled off, and then 3.03 g (15 mmol) of 2-bromoethylphenyl ether obtained in the above (1) was slowly dropped into the reaction solution while heating at 120° C. After completion of dropping, the reaction solution was reacted at the same temperature for another 1 hour while stirring and then filtrated. The filtrate obtained was concentrated and purified by using a column chromatography to obtain 952.6 mg (4.21 mmol) of a desired triethylene glycol monophenyl ether (yield 28%).

(3) Synthesis of the Carrier of the Present Invention in Which a —$CH_2O$ $(CH_2CH_2O)_3Ph$ Group is Introduced By the same manner as in (2) of Example 1 except that 22.6 mg of triethylene glycol monophenyl ether obtained in the above (2) was used instead of 2-phenoxy ethanol, 15.5 g of carrier of the present invention in which a —$CH_2O$ $(CH_2CH_2O)_3Ph$ group was introduced were obtained (yield 47%).

Example 3

Synthesis of the Carrier of the Present Invention (1) Synthesis of pentaethylene glycol monophenyl ether With petroleum ether was washed 564.8 mg of sodium hydride, and then dried under a reduced pressure. After drying, 2.73 g of tetraethylene glycol and 10 ml of tetrahydrofuran were added thereto in an ice bath and reacted while stirring. After generation of hydrogen stopped, 5 ml of tetrahydrofuran dissolving 1.42 g (7.06 mmol) of 2-bromoethylphenyl ether obtained in the above (1) of Example 2 was slowly dropped into the above reaction solution. After completion of dropping, the reaction solution was stirred at room temperature for another 18 hours, the reaction was terminated by adding methanol. After completion of the reaction, the solvent was concentrated under a reduced pressure and the crude product obtained was purified by using a column chromatography, to obtain 515.6 mg (1.64 mmol) of a desired pentaethylene glycol monophenyl ether (yield 23%).

(2) Synthesis of the Carrier of the Present Invention in Which a —$CH_2O$ $(CH_2CH_2O)_5Ph$ Group is Introduced By the same manner as in (2) of Example 1 except that 22.6 mg of pentaethylene glycol monophenyl ether obtained in the above (1) was used instead of 2-phenoxy ethanol, 15.5 g of the carrier of the present invention in which a —$CH_2O$ $(CH_2CH_2O)_5Ph$ group was introduced were obtained (yield 47%).

Example 4

Production of the Osmium Oxide Carried by the Carrier of the Present Invention

To 20 ml of cyclohexane were added 1 g of the carrier of the present invention obtained in Example 1, followed by adding 200 mg of osmium tetroxide thereto while stirring at 50–60° C. and reacting them for about 1 hour while stirring. After the reaction solution was cooled down to room temperature by stop heating, methanol was slowly added to the reaction solution while stirring and then left for standing for about 24 hours. After the product was solidified, filtered, washed with methanol and dried to obtain 1.12 g of the osmium tetroxide carried by the carrier of the present invention (yield 100%) (Amount of osmium tetroxide carried: 10.8%).

Example 5 and 6

Production of the Osmium Oxide Carried by the Carrier of the Present Invention

By the same manner as in Example 4 except that each of the carriers obtained in Examples 2 and 3 was used instead of the carrier of the present invention obtained in Example 1, each of desired osmium tetroxides carried by the carrier of the present invention, respectively, were obtained.

Example 7

Asymmetric Dihydroxylation Reaction

To 3.5 ml of a water-acetone (1:1) solvent were added 66.6 mg of the osmium oxide carried by the carrier of the present invention obtained in Example 4, 21.5 mg of 1,4-bis(9-o-dihydroquinidil)phthalazine, 362.2 mg of potassium ferricyanide and 152.0 mg of potassium carbonate, followed by reacting at 30° C. for 1 hour while stirring. And 59.0 mg of trans-β-methylstyrene dissolved in 1.5 ml of a water-acetone (1:1) solvent were added to the reaction solution and followed by reacting for another 2 hours while stirring. And further, 362.2 mg of potassium ferricyanide and 152.0 mg of potassium carbonate were added to the reaction solution and followed by reacting for another 2 hours while stirring. After the reaction was terminated by adding methanol, the filtrate obtained by filtrating the reaction solution was concentrated to some extent. The obtained product was dissolved in 5 ml of methylene chloride and filtrated using Celite. The filtrate was concentrated and purified using a silica gel thin-layer chromatography, to obtain 70.6 mg of a desired diol, 1-phenyl-1,2-propane diol (yield 85%) (97% ee).

The osmium tetroxide carried by the carrier of the present invention obtained by filtration was washed with water and methanol and recovered quantitatively by drying using a vacuum pump.

Examples 8 and 9

By the same manner as in the above Example 7 except that each of the carried osmium tetroxide obtained in Examples 5 and 6 was used instead of the osmium tetroxide carried by the carrier of the present invention, trans-β-methylstyrene was oxidized and the same compound as the diol compound obtained in Example 7 was respectively obtained.

Example 10

The same reactions as in Example 7 were repeated using the osmium tetroxide carried by the carrier of the present invention which was recovered in Example 7. Yield and optical yield of the diol compound obtained by each reaction are shown in Table 1.

TABLE 1

|  | Number of Repeated Use | | |
| --- | --- | --- | --- |
|  | 1 | 2 | 3 |
| Yield % | 45 | 50 | 50 |
| Optical Yield % ee | 97 | 96 | 96 |

As apparent from Table 1, it can be understood that the osmium tetroxide carried by the carrier of the present invention does not lose its activity as a catalyst in repeated use.

Comparative Example 1

By the same manner as in Example 7 except that the osmium tetroxide carried by the carrier obtained by using only polystyrene, an asymmetric oxidation of trans-β-methylstyrene was conducted. Yield and optical yield of the same diol compound as obtained in Example 7 were 30% and 40% ee, respectively.

As apparent from the results of Example 7 and Comparative Example 1, it can be understood that the osmium oxide carried by the carrier of the present invention enables to obtain an optically active diol compound more easily and in a higher yield, compared to a conventional microcapsulated osmium oxide, in an asymmetric dihydroxylation reaction in a heterogeneous solvent system using potassium ferricyanide as a co-oxidizing agent. In other words, it can be understood that the osmium oxide carried by the carrier of the present invention works very effectively even in a heterogeneous solvent system because it has a hydrophilic group in the structure of the molecule thereof.

Example 11

Carbonyl-forming Reaction of an Olefin

A mixture of 53.9 mg of the osmium oxide carried by the carrier of the present invention obtained in Example 4 (containing 11.8% of osmium tetroxide), 235.3 mg of sodium periodate and 200 mg of molecular sieves 4A (Fine powder, made by Aldrich Inc.) was homogenized by stirring at 60° C. And to the mixture was added 0.5 mmol of trans stilbene and 1 ml of a mixed solvent of water-acetone (1:1), and followed by reacting at 60° C. for 12 hours while stirring. After completion of the reaction, excess hexane was added to the reaction solution and then cooled to a room temperature followed by stirring for another 30 minutes. The reaction solution was filtrated, and the filtrate was washed with hexane and methanol, and extracted with methylene chloride. The extraction was analyzed by a gas chromatography, and it was proved that benzaldehyde was obtained as the reaction product in 95% yield.

Further, a filter cake obtained by filtration was washed with water and methanol, and remaining molecular sieve 4A was removed therefrom, followed by drying under a reduced pressure to recover quantitatively the osmium oxide carried by the carrier of the present invention.

Examples 12–14

The same manner as in Example 11 was repeated using the osmium tetroxide carried by the carrier of the present invention which was recovered in Example 11. Yields of benzaldehyde obtained by each reaction are shown in Table 2.

TABLE 2

|  | Number of Repeated Use | | | |
| --- | --- | --- | --- | --- |
|  | 1 | 2 | 3 | 4 |
| Yield % | 95 | 96 | 97 | 96 |

As apparent from Table 2, it can be understood that the osmium tetroxide carried by the carrier of the present invention does not lose its activity as a catalyst in repeated use.

INDUSTRIAL APPLICABILITY

The osmium oxide carried by the carrier of the present invention can be handled without paying special attention to toxicity or the like even at a high content thereof, and the effect of the osmium oxide itself is stably shown for a long period because the osmium oxide is carried by the carrier. And the osmium oxide carried by the carrier of the present invention has the advantages of having a superior durability and solvent resistance, hardly decreasing its activity in repeated use even for many times, being recovered quantity after use and enabling itself to repeat reuse.

That is, the osmium oxide carried by the carrier of the present invention is very useful as a catalyst for various reactions.

In addition, the osmium oxide carried by the carrier of the present invention can be used advantageously in the industry as an oxidizing catalyst or an oxidizing agent in various chemical reactions such as a dihydroxylation reaction or a carbonyl-forming reaction of a compound having a reactive double bond. Since the osmium oxide carried by the carrier of the present invention has a group having hydrophilic property, on an oxidation reaction and an asymmetric oxidation reaction, particularly in a heterogeneous solvent system, the osmium oxide carried by the carrier of the present invention enables to produce a diol compound easily and in a high optical yield. And the osmium oxide carried by the carrier of the present invention can be used safely and effectively even for an oxidation reaction etc. with using a compound which has been difficult to react in a nonaqueous solvent.

What is claimed is:

1. A carrier for carrying an osmium oxide comprising a polyolefin with an aromatic side group having a group shown by the general formula [1] as a substituent on the aromatic ring of said polyolefin with an aromatic side group:

—A'—O(—A—O)$_n$—R      [1]

(wherein, A is an alkylene group; A' is a bond or an alkylene group; R is an aryl group; and n is an integer of 1 to 10).

2. The carrier for carrying the osmium oxide according to claim 1, wherein A and A' are each independently an alkylene group of 1 to 6 carbon atoms; R is a phenyl group; and n is an integer of 1 to 5.

3. The carrier for carrying the osmium oxide according to claim 1, wherein said polyolefin in the polyolefin with the aromatic side group is a homopolymer or a copolymer of styrene or styrene has that an alkyl group of 1 to 4 carbon atoms as a substituent in the α-position of the styrene.

4. An osmium oxide carried by the carrier according to claim 1.

5. A method for producing an osmium oxide carried by a carrier which comprises contacting the carrier according to claim 1 with said osmium oxide.

6. A method for preventing the activity of osmium oxide from decreasing which comprises combining the osmium oxide on the carrier according to claim 1.

7. A method for producing a corresponding diol compound which comprises reacting a compound having a —C=C— double bond with the osmium oxide according to claim 4.

8. The method according to claim 7, wherein the compound having a —C=C— double bond is an olefin.

9. The method according to claim 8, wherein the olefin is an asymmetric olefin or a trans isomer of a symmetric olefin.

10. A method for producing a corresponding carbonyl compound which comprises reacting a compound having a —C=C— double bond with the osmium oxide according to claim 4 and a strong oxidizing agent.

11. The method according to claim 10, wherein the compound having a —C=C— double bond is an olefin.

12. The method according to claim 10 or 11, wherein the amount of the strong oxidizing agent to be used is 2 or more times by mole relative to an amount of the compound having a —C=C— double bond.

13. The method according to claim 10 or 11, wherein the amount of the strong oxidizing agent to be used is 2 to 4 times by mole relative to an amount of the compound having a —C=C— double bond.

14. The method according to claim 10 or 11, wherein the strong oxidizing agent is a periodate.

* * * * *